(12) United States Patent
Aper et al.

(10) Patent No.: US 10,500,306 B2
(45) Date of Patent: Dec. 10, 2019

(54) METHOD AND DEVICE FOR PRODUCING A BIOARTIFICIAL TISSUE CONSTRUCT

(71) Applicant: Medizinische Hockschule Hannover, Hannover (DE)

(72) Inventors: Thomas Aper, Hannover (DE); Mathias Wilhelmi, Isernhagen (DE); Axel Haverich, Hannover (DE)

(73) Assignee: MEDIZINISCHE HOCHSCHULE HANNOVER, Hannover (DE)

(*) Notice: Subject to any disclaimer, the term of this patent is extended or adjusted under 35 U.S.C. 154(b) by 438 days.

(21) Appl. No.: 14/367,247

(22) PCT Filed: Dec. 20, 2012

(86) PCT No.: PCT/EP2012/005287
§ 371 (c)(1),
(2) Date: Jun. 20, 2014

(87) PCT Pub. No.: WO2013/091865
PCT Pub. Date: Jun. 27, 2013

(65) Prior Publication Data
US 2014/0343662 A1    Nov. 20, 2014

(30) Foreign Application Priority Data
Dec. 23, 2011  (DE) .................... 10 2011 122 227

(51) Int. Cl.
*B29C 41/20* (2006.01)
*A61L 27/22* (2006.01)
(Continued)

(52) U.S. Cl.
CPC ............ *A61L 27/225* (2013.01); *A61F 2/062* (2013.01); *A61F 2/07* (2013.01); *A61F 2/90* (2013.01);
(Continued)

(58) Field of Classification Search
CPC ......... A61F 2/062; B29C 41/38; B29C 41/04; B29C 41/042; B29C 41/045
(Continued)

(56) References Cited

U.S. PATENT DOCUMENTS 5,492,826 A    2/1996  Townsend
5,585,007 A   12/1996  Antanavich et al.
(Continued)

FOREIGN PATENT DOCUMENTS

DE    199 15 610 A1   10/2000
DE    695 20 375 T2    9/2001
(Continued)

OTHER PUBLICATIONS

Sulzer AG, "Process for manufacturing porous tubular plastic prostheses charged with living cells", EP 462051 A, Dec. 18, 1991, Machine Translation.*

*Primary Examiner* — Galen H Hauth
(74) *Attorney, Agent, or Firm* — W&C IP

(57) ABSTRACT

The tissue construct with viable cells in an extracellular matrix made of fibrin is produced with a special method, in which a matrix material and cells are shaped into a hollow body, in particular a tubular hollow body, by means of a rotational casting method in a hollow mould (1), the method comprising the following steps: (a) introduction of cells of at least one cell type and/or a fibrinogen preparation into the rotating hollow mould (1) with the aid of an applicator (4), said applicator (4) being displaced along the rotational axis during the introduction and step (a) being performed one or more times; (b) continuation of the rotation process until the fibrinogen solidifies into a dimensionally stable matrix, obtaining a primarily solidified tissue construct; (c) removal
(Continued)

of the tissue construct from the mould. The construct can also he obtained in a relatively short time from autologous materials.

20 Claims, 3 Drawing Sheets

(51) Int. Cl.
*A61L 27/38* (2006.01)
*A61L 27/50* (2006.01)
*C12M 3/00* (2006.01)
*A61F 2/06* (2013.01)
*A61F 2/07* (2013.01)
*A61F 2/90* (2013.01)
*A61L 27/06* (2006.01)
*B29C 41/04* (2006.01)
*B29C 41/36* (2006.01)
*B29C 41/38* (2006.01)
*B29K 101/00* (2006.01)
*B29L 31/00* (2006.01)

(52) U.S. Cl.
CPC .......... *A61L 27/06* (2013.01); *A61L 27/3804* (2013.01); *A61L 27/3808* (2013.01); *A61L 27/3826* (2013.01); *A61L 27/3834* (2013.01); *A61L 27/507* (2013.01); *B29C 41/04* (2013.01); *B29C 41/36* (2013.01); *B29C 41/38* (2013.01); *C12M 21/08* (2013.01); *C12M 23/48* (2013.01); *B29K 2101/00* (2013.01); *B29K 2901/00* (2013.01); *B29K 2905/00* (2013.01); *B29L 2031/753* (2013.01)

(58) Field of Classification Search
USPC .......................................... 264/310, 311, 503
See application file for complete search history.

(56) References Cited

U.S. PATENT DOCUMENTS

| | | | |
|---|---|---|---|
| 2002/0042128 A1* | 4/2002 | Bowlin | A61L 15/32 435/366 |
| 2004/0005423 A1* | 1/2004 | Dalton | B29C 39/006 428/36.9 |
| 2004/0115176 A1* | 6/2004 | Swartz | A61L 27/225 424/93.7 |
| 2007/0141232 A1* | 6/2007 | Tochterman | B05B 13/02 427/2.25 |
| 2009/0181448 A1 | 7/2009 | Fan et al. | |
| 2010/0040584 A1* | 2/2010 | Melero-Martin | A61K 35/28 424/93.7 |
| 2010/0221304 A1 | 9/2010 | Tan et al. | |
| 2011/0033918 A1 | 2/2011 | Asnaghi et al. | |
| 2011/0245908 A1 | 10/2011 | Papp | |
| 2012/0253456 A1* | 10/2012 | Shin | C12N 5/0691 623/1.42 |

FOREIGN PATENT DOCUMENTS

| | | |
|---|---|---|
| DE | 699 36 582 T2 | 4/2008 |
| DE | 698 38 457 T2 | 6/2008 |
| EP | 0 320 441 A1 | 6/1989 |
| EP | 0 363 310 A1 | 4/1990 |
| EP | 0 462 051 A1 | 12/1991 |
| EP | 0 592 242 A1 | 4/1994 |
| WO | 1993/001843 | 2/1993 |
| WO | 2000/032207 | 6/2000 |
| WO | 2003/032207 | 6/2000 |
| WO | 2003/089566 | 10/2003 |
| WO | 2006/099016 | 9/2006 |
| WO | 2008/137234 | 11/2008 |

* cited by examiner

Flowchart of tissue construct production

Flowchart of automated production

METHOD AND DEVICE FOR PRODUCING A BIOARTIFICIAL TISSUE CONSTRUCT

The invention relates to a method for producing a tissue construct containing viable cells in an extracellular matrix, here also termed a bioartificial tissue construct, an associated device for production thereof, the tissue construct itself, and use thereof.

A "bioartificial tissue construct" is taken to mean a product which is formed from a matrix material and differentiated and/or undifferentiated cells. As matrix material, a material is preferred as also occurs in nature in extracellular matrices of tissues and is also termed intercellular substance. Such artificially generated cell-matrix composites are used instead of synthetic materials as tissue replacement in the bodies of patients, and there, on account of the biological substances which are identified by the body as immunologically acceptable or even autologous substances, can be readily accepted by the bodies of patients and incorporated and reshaped therein.

The invention relates to the production of tissue constructs, as described above, that is to say "tissue engineering". An important field of work is there the production of vessel prostheses for replacing damaged arterial or venous sections, and of bypass materials, that is to say tubular structures which can replace vessels. A further field of work relates in general to the production of tissue patches which are used at the most varied sites of the human or animal body for augmenting or replacing tissue.

DE 199 15 610 A1 discloses a method for colonizing, with biological cells, tubular substrates made of a decellularized allogeneic extracellular matrix. The use of a decellularized allogeneic material, here a collagen matrix, requires that suitable sources of the allogeneic material are available. These are frequently burdened with problems with respect to immunological compatibility.

In the article "Autologous Blood Vessels Engineered from Peripheral Blood Sample" T. Aper et al., Eur. Vasc. Endovasc. Surg. 33, 33-39 (2007), in contrast, the production of a blood vessel made of purely autologous material is described, wherein the extracellular matrix is formed from a fibrin which was obtained from a blood sample of the patient. The cells desired for the vessel prosthesis are, in this case, mixed with the autologous fibrinogen preparation, cast in tubular shapes and allowed to solidify. This takes place via crosslinking of the fibrinogen to form fibrin within the two-component preparation which, in addition to fibrinogen, contains thrombin to initiate the crosslinking. The casting must proceed rapidly, since the fibrinogen preparation is only workable for a limited time. Astonishingly, it has been found that the cells organize themselves within the tubular structure itself and result in a satisfactory vessel prosthesis. Problems still exist with the stability of the resultant cast prosthesis and with the production time.

The object underlying the invention is to provide an improved tissue construct containing viable cells in a fibrin matrix which can be obtained in a relatively short time even from materials which are autologous with respect to the intended recipient, and which has a structure similar to the natural pattern which is accessible to remodeling in the body of the recipient.

To achieve this object, a method according to claim 1, an associated device according to claim 9, a tissue construct according to claim 14, and use thereof according to claim 17 are provided.

The method according to the invention is one in which a matrix material and cells are molded by means of a rotary casting method in a hollow mold to give an, in particular, tubular hollow body. Depending on the geometry of the hollow mold, that is to say the inner surface thereof, on which the cast hollow body is formed, a tubular construct is obtained when the hollow mold is substantially tubular, whereas, for example, a bubble-shaped construct is obtained when the hollow mold is more spherical or sac-like and, in particular, when it is in this case open at only one end.

Rotary casting methods are known as such, and need not be described here in detail. They have been used for a long time in plastics technology for production of hollow parts. Liquid plastic is introduced in injection molding into a rotary mold in such a manner that a plastic film is formed on the inner wall of the hollow body. After demolding, a hollow body is obtained. The techniques known from these methods are applicable to the invention.

In the invention, a liquid matrix material and cells are introduced into the hollow mold provided for the tissue construct and molded to form a hollow body in rotary casting. As matrix material, a fibrinogen preparation is used which is crosslinked to form a fibrin matrix. The fibrinogen preparation can consist of a plurality of separated components which are first combined during the application into the hollow mold, or immediately before. The cells are used as a cell suspension directly from a cell culture or from a cell sorting fraction. They can be obtained from blood tissue or fat tissue or other sources, various methods are known therefor. Preference is given to autologous cells, and likewise to autologous fibrinogen. The fibrinogen can be obtained from blood or blood plasma. Suitable methods therefor are likewise known to those skilled in the art.

"Fibrinogen", here, denotes any composition that is crosslinkable or polymerizable to form a fibrin. The conversion of fibrinogen to fibrin takes place naturally in blood clotting. This is a reaction cascade which effects clotting—an aggregation of blood components—and thereby effects a wound closure. Fibrin glue, that is to say polymerized fibrinogen, is used in surgery, both intracorporeally and in external wound care. Commercial fibrin glues are known and are described, for example, in U.S. Pat. No. 5,585,007 A and EP 0 592 242 B1.

All non-crosslinked forms of fibrin here are summarily designated fibrinogen. This can be non-crosslinked fibrin I or non-crosslinked (dissolved) fibrin II. Also, crosslinked fibrin types can be redissolved by particular agents, and then again used as fibrinogen. The fibrinogen is crosslinked, for example, using thrombin, calcium ions and activation factor XIII. Factor XIII is activated by thrombin in the presence of calcium ions. Crosslinked fibrin II is produced from fibrin (monomer), or generally from a fibrinogen.

A "fibrin preparation", in the context of this invention, is taken to mean a fibrinogen formulation which was mixed with a crosslinking agent immediately before use in step a) of the method, or which is freshly mixed during the application. The fibrinogen preparation which was obtained from at least two components shortly before use, is introduced with the aid of the applicator rapidly into the rotary hollow mold and crosslinked there in the applied layer without delay during the rotation within a maximum of 10 minutes, preferably a maximum of 5 minutes, and, in the particularly preferred examples, within approximately 2 to 3 minutes. In the examples, a commercially available fibrinogen solution is mixed with thrombin, calcium salt solution and protamine to antagonize heparin and form a pH balance. The pH of the fibrinogen preparation is adjusted to a physiological value.

Cells and matrix material can be layered sequentially or introduced in a mixture or in layers of different mixtures.

The matrix material for this purpose must be liquid or pourable. The matrix material must be processed promptly, since it is crosslinked to form a fibrin matrix during the process. The fibrinogen preparation is generally a two-component preparation of fibrinogen monomers and a crosslinking or clotting agent, as explained in more detail hereinafter. One of the components can be premixed with the cells.

The method comprises the following steps:

(a) Introducing cells of at least one cell type and/or a fibrinogen preparation with the aid of an applicator into the rotating hollow mold, wherein the applicator during the introduction is shifted along the axis of rotation and wherein step a) is carried out once or several times.

The material is introduced into the rotating mold, that is to say first, the mold is started in rotation empty. Previously, or thereafter, an applicator is introduced into the mold in such a manner that cells and/or the single- or multicomponent fibrinogen preparation are delivered into the already rotating hollow mold. The applicator during the introduction of the material is shifted along the axis of rotation in such a manner that the material, i.e. the cells and/or the fibrinogen preparation are distributed evenly in the hollow mold. This step can be carried out once or several times. In the case of a single introduction according to step a), a mixture of cells and fibrinogen preparation, namely fibrinogen and crosslinker, is used. As a result an even layer of fibrin and cells of at least one cell type is formed. This method is suitable for simple constructs. Generally, it is intended that step a) is carried out several times. In a multilayer structure, it is possible, to introduce layers solely of fibrinogen preparation, for example as intermediate layers, or as lining of the hollow mold, or, according to a further variant, layers solely of a cell suspension which are brought in a thin layer on or between fibrin layers. As a result of the constant rotation of the mold, the layers during application are sufficiently dimensionally stable. The cells are bound into the solidifying fibrin matrix still during the rotation period.

Preferably, it is intended that at least one cell type or one cell fraction which can be suspended in culture solution or blood plasma, is introduced in a mixture with or simultaneously with the fibrinogen preparation. Culture solutions can contain further components such as, e.g., growth factors. The cells can also be applied in a mixture with a component of an at least two-component fibrinogen preparation, especially, then, preferably simultaneously with a non-fibrin-containing component. It is particularly preferred to mix one or more cell types in advance with the crosslinking agent for the fibrinogen and to apply this mixture simultaneously with the fibrinogen, for example with the aid of an application via a mixing chamber fed with two feed lines. Preferably, a plurality of repetitions of step a) for a plurality of layers are carried out, which at the end of the method in each case consist of fibrin matrix and a defined cell type present therein.

The expression "cell type" is taken in this case to mean that it can be both a cell population having defined characteristics and preferably a prevailing cell type such as, for example, endothelial cells, muscle cells or fibroblasts, or undifferentiated cells such as, for example, endothelial precursor cells from one or more of the abovementioned cell sources.

b) Continuing the rotary process up to solidification of the fibrinogen to form a dimensionally stable matrix, obtaining a primary-solidified tissue construct. Also after completion of the application process, with the aid of the applicator, the rotation is continued until a fibrin matrix has resulted from the fibrinogen preparation by crosslinking or polymerization or clotting. A dimensionally stable matrix in this case is taken to mean one that is no longer free-flowing, or at least no longer spontaneously free-flowing, i.e. which after switching off the rotary drive, when the hollow mold has come to a standstill, retains its outer shape and form for a certain time further. The product obtained immediately after completion of the method is termed a primary-solidified tissue construct which, in contrast to a construct that is bioartificially generated over a relatively long time period, for example in a bioreactor, previously consists only of crosslinked fibrin—the fibrin matrix—and single cells present, i.e. embedded, therein. The cells have not yet expanded further up to this time point and, in the case of use of previously undifferentiated cells, not yet differentiated further.

c) Demolding the tissue construct. The dimensionally stable primary-solidified tissue construct can consequently be demolded. The rotationally symmetrical construct is removed and optionally further processed. For example, a tubular tissue construct obtained can be cut open laterally and thus made into a flat tissue construct. Generally, the rotationally symmetrical constructs can be converted into flat constructs by separation or division, which flat constructs correspond to the entirety or to a part of their original shell surface. In this manner, using the method, tissue patches and, for example, skin replacement pieces, may be obtained.

A particular advantage of the method is in its speed. Two-component fibrinogen preparations, as are known, for example, for wound care, crosslink very rapidly, which made their previous use in methods for producing bioartificial tissue seem not very expedient. Via the layer application according to the invention into the rotating hollow mold in a thin, optionally multiple, layer application, a targeted geometry can be built up very rapidly. For example, it is possible to build up and solidify a tubular structure of approximately 15 cm in length and 6 mm in diameter in the course of only two to three minutes. Preferably, the solidification times for the individual layers are below five minutes, more preferably below three minutes. After completion of the application processes, the rotation of the mold is continued for at least 5 to 10 minutes. For safety, in the example a rotation time of 20 minutes after completion of the material introduction is provided.

As already described above, in particularly preferred embodiments, a plurality of cell types are used simultaneously or sequentially. The cell types in this case are selected, in particular, from the group: fibroblasts, fibrocytes, muscle cells such as, in particular, SMC or SPC, endothelial cells (EC) such as, in particular, EPC, also including EOEC. Also, fat tissue-associated cells, such as, for example, adipose tissue derived (stem) cells (ASC) can be used. These cell types, as already described above, are preferably introduced into the rotating hollow mold within a fibrinogen preparation, and particularly preferably in a mixture with a component of a fibrinogen preparation, or simultaneously with the fibrinogen preparation, in such a manner that with each introduction of a new cell type a layer of fibrin matrix with cells embedded therein is formed.

The currently preferred examples comprise (a) the successively following application steps: introduction of 1. fibroblasts, 2. smooth muscle cells and 3. endothelial cells in this sequence from the outside, i.e. from the hollow mold wall, towards the interior, i.e. towards the hollow mold center, (b) the simultaneous application of ASC and ES or (c) the sole use of ASC.

The fibrinogen preparation and/or the cells are preferably introduced by spraying and particularly preferably in a layer thickness less than or equal to 1 mm, and more preferably less than or equal to 0.5 mm. For the spray application, the applicator is equipped with a spray head, i.e. a nozzle, at the application head—the point at which the cells and/or the fibrinogen are delivered into the rotating mold.

Preference is given in general in this method to individual layer thicknesses up to 0.4, and more preferably up to 0.3 mm. The total layer thickness of a single- or multilayer construct preferably totals up to 3 mm, more preferably up to 2 mm, and in other embodiments up to 1 mm, depending on the desired tissue piece.

In preferred embodiments, the cells are introduced while a rotation of between 100 g and 650 g is carried out, which, at the customary sizes of vessel prostheses, corresponds to speeds of rotation of up to 6000 rotations per minute.

In addition, it is provided according to a preferred embodiment, that, before the start of the introduction of cells and/or fibrinogen, or between a plurality of steps according to step a) of the method according to the invention, in addition a support frame is used. The support frame or support grid preferably consists of metal and has, in particular, the shape of a metal grating lining the hollow mold at the site of application. The metal can be a nickel-titanium alloy, and in particular Nitinol⊙. As material, a metal grid "gSVS⊙ Mesh" from Kips Bay Medical Inc., USA, is suitable for example. Also, materials which are used for vessel stents, are shaped in a grid or grating type, of metal alloys or plastic, can be used here. The support frame facilitates the immediate implantation of the primary-solidified tissue construct, very particularly when this cannot be further prepared by a further treatment, for example in a bioreactor, for later implantation.

Alternatively, or additionally, it is possible to subject the demolded tissue construct to a post-treatment, for example in a bioreactor. For this purpose, for example, a tubular primary-solidified tissue construct can be clamped into a bioreactor suitable therefor and there post-treated. This can also proceed under nature-similar pulsed or continuous flow conditions. The resultant primary-solidified tissue construct is then stabilized during a treatment time of hours up to weeks and obtains a higher tensile strength. For the after-treatment, for example, the abovementioned reactor according to DE 199 15 610 A1 is suitable.

The tissue construct can be post-treated after demolding, as described above, or it can be first left in the mold and treated luminally.

The invention further comprises a device suitable for carrying out the method.

Rotary casting methods are known as such from plastics technology and do not need to be described in more detail here. They are methods in which the hollow mold is rotated about an axis during the injection or casting of the (injection) molding composition, in such a manner that the material during casting is sprayed or centrifuged onto the inner wall of the hollow mold, cured there, and forms a hollow body. The hollow mold can in principle have any desired rotationally symmetrical shape. It can be spherical, in order to generate a bubble, but in a preferred case, it is tubular, wherein the cross section of the tube can vary, in order, for example, to generate a vessel having a non-uniform vessel diameter.

The hollow mold can, for example, consist of a tube open at one end or at both ends. In the examples, a metal tube is used which is lined with Teflon, or into which two Teflon hemispheres are inserted which together form the internal hollow mold. During demolding, the latter facilitates the removal of the freshly formed tissue construct.

In order to drive the rotatable hollow mold, a rotary drive is provided. For this purpose the hollow mold is generally connected to a motor via a shaft for co-rotation. The device further comprises feed lines for liquid cell and fibrinogen preparations which open out into a mixing head of an applicator, and also guide means for a movement of the applicator with an associated application head along the axis of rotation of the hollow mold. The applicator can preferably consist of a tube having an application head, via which the materials can be delivered in a site-accurate manner. In the preferred case, the application head is a nozzle, and a spray application proceeds. Alternatively, the materials are delivered in a thin jet or dropwise and are distributed in the mold by the action of centrifugal forces. The applicator is moved along the axis of rotation, which effects a uniform layer application. This is particularly important in the case of elongate and tubular hollow molds. The axis of rotation, in particular in the tubular hollow mold, is preferably positioned horizontally. The device further comprises preferably associated open-loop and closed-loop control means for delivery of the liquid materials via the feed lines, the open-loop control of the mixing operation, the open-loop control of the amount of the materials applied and the application time, the advance of the applicator during the entry and exit, and also open-loop or closed-loop control of the speed of rotation.

Applicators are known in the prior art. Those which are usable or adaptable here are, for example, applicators as are shown in DE 698 38 457 T2 or DE 699 36 582 T2.

In a preferred embodiment, the hollow mold is constructed to be hollow cylindrical or tubular. It is further preferably coated on the inner surface thereof with Teflon or equipped with a detachable Teflon insert which can be constructed in multi-piece form, in order to facilitate demolding.

The device can additionally comprise in a preferred embodiment an apparatus for generating a fibrinogen preparation from blood or fat tissue. In the prior art, methods are known with which fibrinogen can be obtained very rapidly from patient's blood, in order thereby to generate fibrin glue in situ. The advantage is that it is an autologous fibrin glue, i.e. blood of the patient is used for which the vessel construct which is obtained according to this method is provided. Within the device according to this invention, therefore, an arrangement can be present which comprises an application as described above, in addition a device for separating off a fibrinogen, for example from plasma, as known, inter alia, from DE 695 20 375 T2 and further documents cited therein, and also storage vessels for the crosslinking agents and an additional site for blood or blood plasma, from which, using this arrangement, within the device according to the invention, the fibrinogen preparation is produced.

In addition, the device according to the invention comprises storage vessels or addition sites and feed lines and also optionally reservoirs for various cell suspensions which are used in the context of the invention. The various cell types to be used in the method can be cultured externally in advance and then introduced into the device according to the invention.

Alternatively, it is also possible that the device contains a cell sorter for providing various cell types obtained from blood and/or fat tissue. The cell sorter delivers the separated cells via feed lines to the applicator. Cell sorters are likewise known in the prior art and need not be described in more detail here.

The method provides an immediate method product which here is termed primary-solidified tissue construct. As already described above, it is possible in the course of a few minutes, to obtain a dimensionally stable structure. The fibrinogen preparation which is obtained from a two-component system of fibrinogen formulations and associated crosslinkers, crosslinks relatively rapidly and becomes dimensionally stable, in such a manner that the cells are rapidly fixed in the applied layers. The crosslinking operation proceeds within a few minutes. A characteristic of the invention is to form a layer of cells and fibrinogen preparation in the rotating mold. Via the centrifugal forces, the cells that are applied in a thin layer are retained in the fibrinogen until the crosslinking has taken place. The rotation is continued until the layer is dimensionally stable. The same applies correspondingly during application of a plurality of layers one above the other. In this manner, the primary-solidified construct receives a cross-sectional structure which can be set in a targeted manner.

The primary-solidified tissue construct consists of a dimensionally stable, i.e. no longer spontaneously free-flowing, fibrin matrix, and cells embedded therein. The tissue construct is rotationally symmetrical, in particular tubular, or was obtained from a rotationally symmetrical first construct by division and possibly joining together a plurality of parts resulting. The original tissue construct can be, for example, cut open on one side and spread out. The surface of the construct then corresponds to the shell shape of the rotary hollow mold. In this case, different cell distributions are situated in two or more layers of the tissue construct. Even when only one layer of cells and fibrinogen is applied with the applicator in the hollow mold, the cells, owing to the effect of centrifugal force, are situated in a preferred plane. In the case of multilayer application of different mixtures, the most various cross-sectional structures are conceivable. Various cells can be separated, for example, by fibrinogen layers, or they can follow sequentially.

According to the particularly preferred embodiments, the tissue construct contains layers of (a) endothelial cells, smooth muscle cells and fibroblasts that are embedded in the fibrin matrix, or (b) only ASC or (c) ASC in a mixture with endothelial cells. The preferred structure, in particular of example (a), is such that the endothelial cells are directed towards the luminal side of a tubular construct.

The tissue replacement piece can be used according to the invention as a prosthetic tissue replacement in a patient body. In the case of a tubular method product, the use as vessel prosthesis or bypass material is provided. If the tissue construct, as obtained from the method, is cut open or divided, flat tissue replacement pieces are obtained which can be used as patches, e.g. as augmentation material. Further uses of the constructs according to the invention are possible.

The tissue construct according to the invention can in addition contain a support frame made of metal or plastic, preferably a metal grating or metal grid.

The invention is described in more detail hereinafter with reference to exemplary embodiments and drawings. In the drawings.

Figure 1:
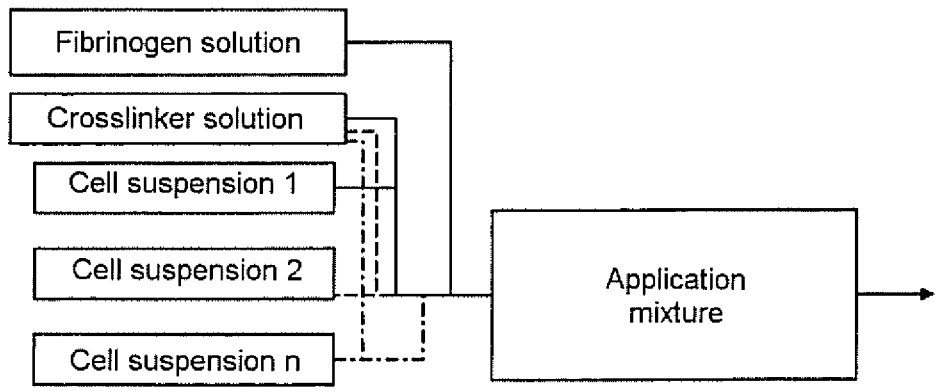
FIG. 1 shows a first flowchart of a tissue construct production

FIG. 1 shows a simplified flowchart for the tissue construct production. The fibrinogen solution and the associated crosslinker solution which together yield the fibrinogen preparation can be mixed in various ways with the cell suspensions obtained from culture. The method procedure cited in this example provides that the cell suspensions are first mixed with crosslinker solution and this mixture is mixed with the fibrinogen solution and immediately applied. First, therefore, the cell suspension 1 is mixed with the crosslinker solution, the mixture is mixed with fibrinogen solution and this mixture is applied in such a manner that a first layer results in the hollow mold. Then, the second cell suspension 2 is mixed with the crosslinker solution, subsequently mixed with the fibrinogen solution and finally applied. A second layer results therefrom, in such a manner that the cells of the second suspension come to lie luminally above those from the first suspension. Finally, an n-th cell suspension is mixed with crosslinker solution, then mixed with fibrinogen solution, and applied to a n-th mixture. The construct has n layers.

The cells can in principle be either autologous, such as also xenogenous, or of allogeneic origin. The fibrinogen can likewise be purely autologous, xenogenous or allogeneic, or synthetic fibrinogen can be used.

Hereinafter an example protocol of a production method according to this flowchart is cited:

(1) Cell Isolation and Culturing

Blood is withdrawn under sterile conditions and mixed with 100 units of heparin per ml of blood. To separate the cells from plasma, the blood is centrifuged for 12 min at 600 g and 30° C. The plasma is pipetted off and, to separate a fibrinogen preparation, frozen for at least 24 hours at −20° C. After taking off the plasma, the monocyte fraction is aspirated and resuspended in equal parts in three vessels in phosphate buffered saline solution (PBS). Centrifugation of the suspensions at 300 g for 7 min at 4° C. Take-off of the supernatant and resuspension of the remaining cell pellets with in each case 10 ml of endothelial cell medium, muscle cell medium or fibroblast medium. Endothelial Cell Growth Medium-2 (EGM-2), Smooth Muscle Growth Medium-2 (SGM-2) and Fibroblast Growth Medium-2 (FGM-2) (in each case from Lonza) are used. The media consist of the respective basal media, to which the respective supplements are added. The suspensions are added to a cell culture flask in each case and incubated at 37° C. and 5 vol % in the incubator cabinet. The first medium change is performed after two days and then every three days.

With the monocyte fraction, precursor cells for endothelial cells and smooth muscle cells and circulating fibroblasts (fibrocytes) are introduced into culture. During the incubation with the respective specific culture medium, on average, after seven days, outgrowth of colony-forming cells occurs.

After reaching the confluence, the cells are detached with trypsin and passaged one to three, that is to say divided from one culture flask to three culture flasks.

The endothelial cell culture in EGM-2 medium is used after the first passage, the muscle cell culture in SGM-2 medium and the fibroblast culture in FGM-2 medium are passaged four to five times.

(2) Generation of a Fibrin Preparation for the Extracellular Matrix
1. After centrifugation of heparinized blood, the plasma is pipetted off and frozen at −20° C. for at least 24 hours.
2. Thawing the frozen plasma first at room temperature and then in the refrigerator to 4° C.
3. Centrifugation of the thawed plasma at 450 g for 3 min at 4° C. with brake.
4. Take-off of the supernatant. The remaining pellet dissolves without further additives at 37° C.
5. The fibrin preparation can be frozen until further use up to 30 days at −20° C.

(3) Generation of a Bioartificial Vessel Replacer
1. Fibrin preparation from (2) is warmed to 37° C.
2. Generation of a thrombin preparation (crosslinker solution), 1 ml consisting of:
   20 units of bovine thrombin
   400 µl of calcium chloride solution (50 mmol/l)
   300 µl of protamine (5000 units/ml)
   300 µl of aprotinin solution (230 000 KIU/ml)
3. Detaching the cells from (1) with trypsin, centrifugation at 300 g for 7 min and resuspension of the
   a) fibroblasts in the thrombin preparation at a cell density of $2\times10^5$ cells per milliliter
   b) muscle cells in the thrombin preparation at a cell density of $1.5\times10^6$ cells per milliliter
   c) endothelial cells in the thrombin preparation at a cell density of $1\times10^5$ cells per milliliter
4. Mixing the fibrin preparation from 1. and the crosslinker solutions or thrombin preparations from 3. mixed with the various cell sorts in each case in the ratio 1:1 for the various steps of the method, that is to say first 1:1 mixture of the fibrin preparation from 1. with the thrombin preparation according to a) by simultaneous feeding by means of a Y connector to the applicator and corresponding procedure for the further method steps by mixing the fibrin preparation with the thrombin preparations according to b) or c), respectively. The application proceeds as described for FIG. 3.

Further Example Details:
Fibrinogen Preparation

As a departure from the preceding example protocol, fibrinogen produced from patient's blood can also be produced using a VIVOSTAT☉ system. The self-crosslinking fibrinogen preparation contains thrombin (5 to 10 IU/ml) and calcium (30 to 40 mmol/l).

Alternative Cell Production

In an alternative method, cell production proceeds by centrifugation, optionally after mechanical tissue comminution, and subsequent cell sorting, e.g. with FACS sorting or magnetic cell sorting using the Miltenyi system (Miltenyi Biotech GmbH, Bergisch Gladbach). Mechanical tissue comminution is only required if fat tissue or other non-liquid tissue is used as cell source. The cell sorts obtained here can be sprayed on as a mixture, or individually, as obtained, as a suspension, or sprayed on in a mixture with the fibrinogen preparation.

Specifications of the Method and the Device
   As hollow mold, by way of example, a brass tube
      Length: 120 mm
      Inner diameter: 10 mm
      Outer diameter: 12 mm
   was used, into which two Teflon hemispheres
      Length: 120 mm
      Outer diameter: 10 mm
      Inner diameter: 8 mm were inserted. The mold was rotated at up to 4000 rotations per minute. The application process was carried out at centrifugal forces between 150 and 330 g.

The applicator is first completely pushed into the casting mold and during the application process moved through the mold at a velocity of approximately 4 to 5 mm/s along the axis of rotation and in this case removed from the casting mold. In total about 1 to 1.2 ml of the solutions are sprayed in the mold, as a result of which a layer about 0.3 to 0.4 mm thick is formed. The process can be repeated several times, in such a manner that a segment having a wall about 1 mm thick overall is formed in the casting mold. In the preferred example, three solutions were sprayed on
1. Fibrinogen preparation in a mixture with fibroblast suspension
2. Fibrinogen preparation in a mixture with suspended smooth muscle cells
3. Fibrinogen preparation in a mixture with suspended endothelial cells.

Each of the layers was sprayed on with about over 0.3 mm layer thickness, and so a preparation having in total about 1 mm layer thickness was formed. After application of the last layer, the rotation in the mold was further continued for 15 to 20 minutes. Thereafter, the casting was demolded.

Via the cell application matched in time to one another, already initially a hierarchical arrangement of the cells is achieved, and via the rotation, a compaction of cells and matrix is achieved.

Figure 2:
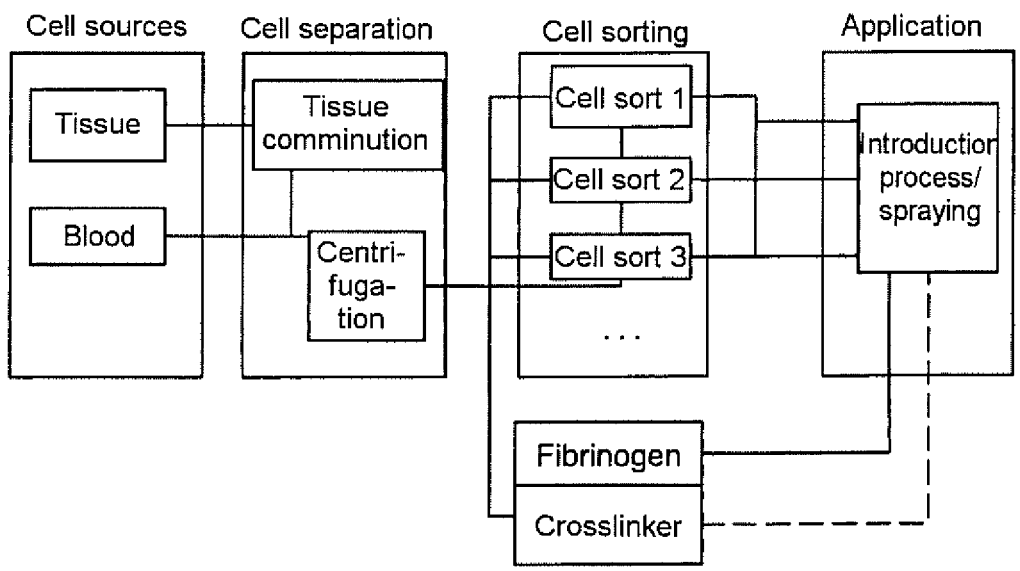
FIG. 2 shows a flowchart of an automated tissue construct production

FIG. 2 shows a flowchart for the automated production of a tissue construct. The substantially automated production according to this example begins with the selection of the cell sources from blood and tissue. Preference is given to the use of autologous blood and fat tissue of the patient for whom the tissue construct is intended. If tissue, for example fat tissue, is used, it is first comminuted and then further treated. The treatment of the fat tissue can in this case follow, for example, the details from WO 2008/137234 A1. The blood and/or the comminuted tissue are centrifuged, the pellet is optionally resuspended.

The resultant cell mixtures are fed to a cell sorter. Cell sorters are known as such. FACS cell sorters, for example, can be used, or those which sort the cells after labeling with magnetic antibodies. The individual steps within the cell sorting, namely labeling, sorting and optionally delabeling, if required, are not shown here. The cell sorter provides various cell fractions for the subsequent application which is continued in principle as described for FIG. 1.

Figure 3:
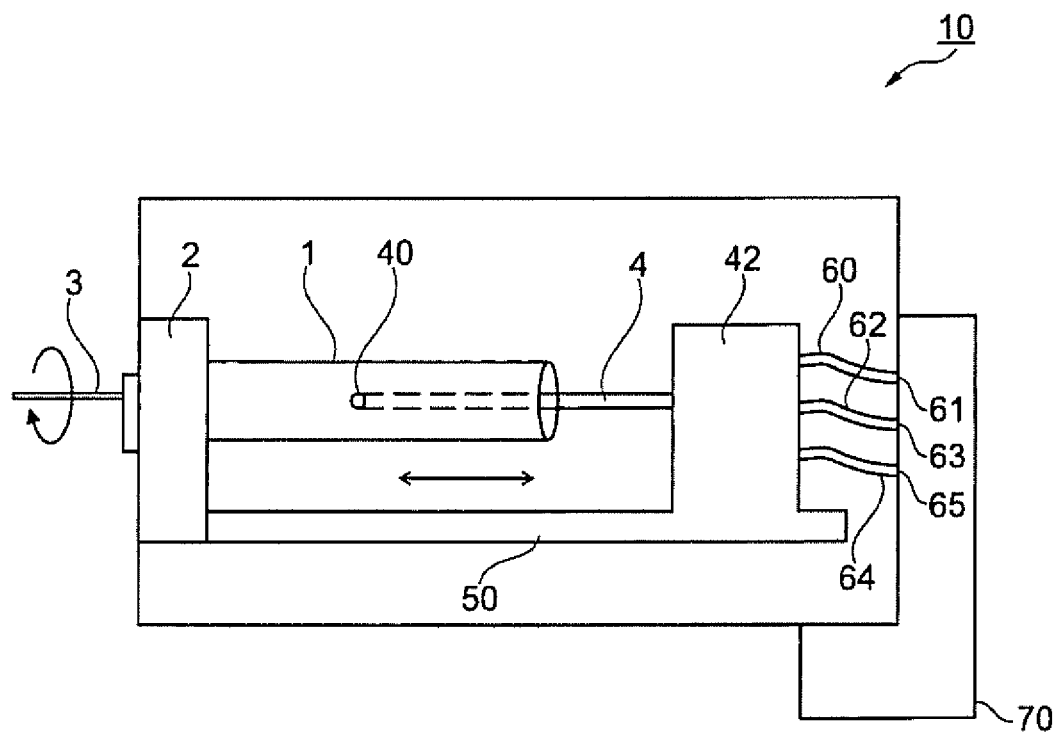
FIG. 3 shows a schematic depiction of a device for producing a tissue construct

FIG. 3 shows a device for producing a tubular tissue construct in cross section at the side. The device designated as a whole with 10 contains a hollow mold 1 in the form of a Teflon-lined metal tube which is conducted through a block 2 and is connected so as to co-rotate with a shaft 3. The rotary motion is indicated by a rotary arrow. The drive motor is not shown in this figure. An applicator 4 is introduced into the hollow mold from the open end of the tubular hollow mold 1. In this example, the applicator 4 has the shape of a thin tube having an opening from which the material supplied can exit and which therefore forms an application head 40. If material exits from the application head 40 while the hollow mold 1 is rotating, it first arrives owing to gravity at a point situated below the application head 40 within the hollow mold 1. However, owing to the simultaneous rotation, the material is applied in an annular shape in the inner space of the hollow mold. As indicated by the double arrow, the applicator 4 can be moved to and fro along the axis of rotation of the hollow mold 1, for which purpose a rail or bench 50 is provided, on which a holder 42 for the applicator 4 is mounted so as to be able to shift longitudinally. By shifting along the longitudinal axis or axis of rotation of the hollow mold 1, the material delivered through the application head 40 is distributed in a spiral shape or successively in adjoining annular regions over the inner wall of the hollow mold 1. The material that is to be distributed, i.e. the cell suspensions and/or cell mixtures and the fibrinogen preparation, from which the layers of the construct that is to be formed are to be composed, are fed via feed lines 60, 62, 64. The number of the feed lines is only selected by way of example. The feed lines open into a mixing chamber of the applicator 4, which mixing chamber is not shown in this figure and is hidden in the holder 42, in order to feed the various materials to the applicator simultaneously and mixed in situ upstream of the application. The materials can either be fed directly into the feed lines via the feed points 61, 63 and 65, e.g. by injection, or the feed lines are supplied from the arrangement 70 which can contain elements which are not shown in detail such as fibrino centrifuges, cell sorters, cell culture storage containers, storage containers for further components such as crosslinker solutions, purge solution and the like, and also open-loop and closed-loop control means and additional mechanical components, such as pumps etc. The application head 40 can also be a spray head, as is shown in more detail in FIG. 4.

Figure 4:
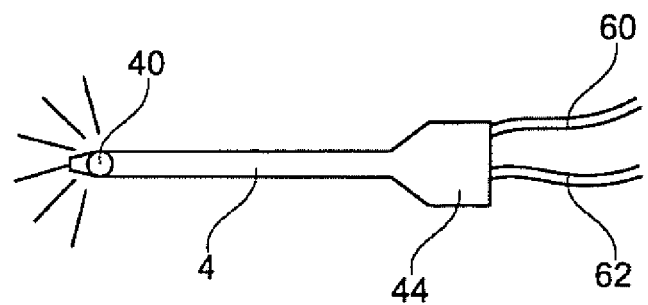
FIG. 4 shows a schematic depiction of an applicator having a spray head

FIG. 4 shows a single applicator 4 having an application head 40 in the form of a nozzle which is suitable to spray finely the supplied solutions having the materials that are to be applied. The applicator 4 in this example shown is supplied with material solutions via two feed lines 60 and 62 which are combined in a mixing chamber 44, mixed, and immediately further transported to the spray head or application head 40, and delivered through this.

Figure 5:
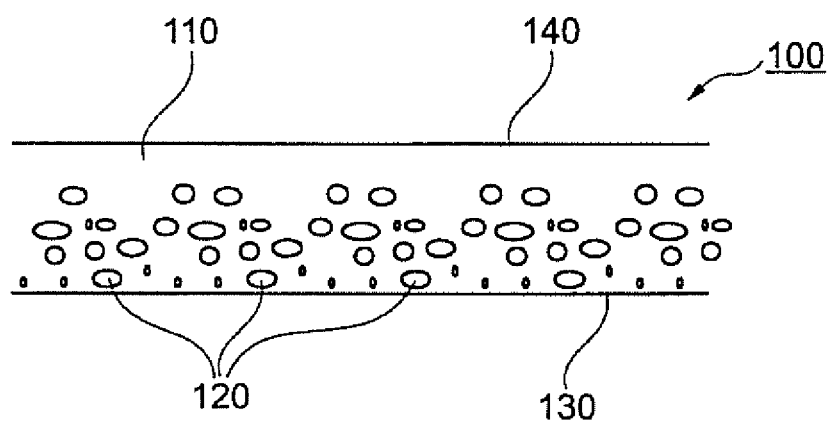
FIG. 5 shows a schematic longitudinal section through a first single-layer tissue construct

FIG. 5 shows a schematic depiction of a longitudinal section through a first, single-layer tissue construct. The drawing is not true to scale and the shape of the cells is only indicated. The tissue construct 100 generated with single-layer application consists of a layer of a fibrin matrix 110 obtained from fibrinogen and crosslinker, in which cells 120 are stored. Owing to the centrifugal forces, the cells have increasingly collected on a side 130 of the layer of the fibrin matrix 110 facing the hollow mold 1 which is not shown here during the production. The cell concentration is therefore not uniform over the cross section. The tissue construct 100 could then before or after demolding, be further treated luminally, wherein, for example, a coating could be applied on the side 140. The construct can also be further treated in a bioreactor which is not shown, wherein, e.g., a flow stimulus can be applied with the aid of flowing culture medium, e.g. luminally along the side 140. Also, for example, from the side 140, uniform or pulsing pressure can be applied to the tissue construct.

Figure 6:
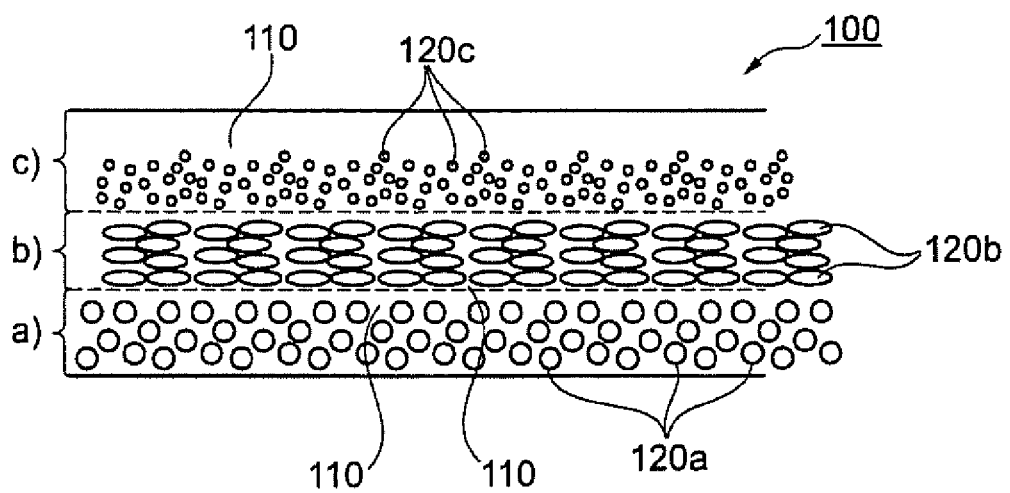
FIG. 6 shows a schematic longitudinal section through a multilayer tissue construct.

FIG. 6 shows a different multilayer tissue construct 100 which consists of the layers a), b) and c). These three layers were applied one over the other in three application processes and contain different cell types 120a, 120b and 120c, which are shown in different shapes, merely for improved differentiation. The portrayal in turn is not to scale, and the cell shape is to be considered arbitrary and purely symbolic. All three layers a), b) and c) consist in turn of the fibrin matrix 110, into which the respective cells 120a to 120c are introduced. As may be seen from FIG. 6, a specially structured construct is obtained directly by the method, without further remodeling, which construct can be reproducing a natural structure. For this purpose, the cells selected in each case for the layers are selected in accordance with the tissue that is to be reproduced and arranged in a fitting concentration and layer thickness.

LIST OF REFERENCE SIGNS

10 Device
1 Hollow mold
2 Block (holder/rotary mount)
3 Shaft
4 Applicator
40 Application head/spray head
42 Holder (for 4)
44 Mixing chamber (of 4)
50 Bench
60 Feed line
61 Feed point
62 Feed line
63 Feed point
64 Feed line
65 Feed point
70 Arrangement (cell production, cell sorting)
100 Tissue construct
110 Fibrin matrix
120 Cells (also 120a, 120b, 120c)
130 (Outer) side of the construct
140 Luminal side of the construct
a)-c) Layers of 100

The invention claimed is:

1. A method for producing a tissue construct containing viable cells in an extracellular matrix, in which a matrix material and cells are molded by means of a rotary casting method in a hollow mold to give a hollow body, having the following steps:
    (a) introducing cells of at least one cell type together with a fibrinogen preparation in a mixture with the aid of an applicator into the rotating hollow mold, wherein the applicator during the introduction is shifted along the axis of rotation and wherein step (a) is carried out once or several times;
    (b) continuing rotation of the hollow mold up to solidification of the fibrinogen to form a dimensionally stable matrix, obtaining a primary-solidified tissue construct; and
    (c) demolding the tissue construct,
    wherein the cells are introduced while a rotation of 100 g to 650 g is carried out.

2. The method as claimed in claim 1, wherein a plurality of cell types are used simultaneously or sequentially.

3. The method as claimed in claim 2, whereby successively following application steps according to step (a), fibroblasts, smooth muscle cells and endothelial cells are used, or in one or more application steps according to step (a), only adipose tissue derived stem cells (ASC), or ASC in a mixture with endothelial cells, are used.

4. The method as claimed in claim 1, wherein the cells are applied in each case in a mixture with the fibrinogen preparation, or simultaneously with the fibrinogen preparation, or in a mixture with a component of the fibrinogen preparation.

5. The method as claimed in claim 1, wherein the cells and the fibrinogen preparation are introduced by spraying.

6. The method as claimed in claim 1, wherein, in the hollow mold, before the start of the introduction of cells and fibrinogen, or between a plurality of steps according to step (a), in addition a support frame is used.

7. The method as claimed in claim 1, wherein a post-treatment of the primary-solidified tissue construct is performed in a bioreactor.

8. The method as claimed in claim 1, wherein the hollow body is a tubular hollow body.

9. The method according to claim 2, wherein the cell types are selected from the group of fibroblasts, fibrocytes, muscle cells, endothelial cells (EC) and cells obtained from fat tissue.

10. The method according to claim 9, wherein the cell types used include muscle cells selected from SMC and SPC.

11. The method as claimed in claim 9, wherein the cell types used include endothelial cells selected from EPC and EOEC.

12. The method as claimed in claim 9, wherein the cell types used include cells obtained from fat tissue, wherein said cells obtained from fat tissue are ASC.

13. The method as claimed in claim 4, wherein the mixture with the cells are applied in each case in a mixture with a fibrinogen cross linking agent.

14. The method as claimed in claim 5, wherein a layer thickness of the cells and the fibrinogen preparation is ≤1 mm.

15. The method as claimed in claim 5, wherein a layer thickness of the cells and the fibrinogen preparation is ≤0.5 mm.

16. The method as claimed in claim 6, wherein the support frame is made of metal or plastic.

17. The method as claimed in claim 6, wherein the support frame is in the form of a grating.

18. The method as claimed in claim 13, wherein an inner surface of the hollow mold is coated with polytetrafluoroethylene or includes a detachable polytetrafluoroethylene insert.

19. The method as claimed in claim 1, wherein the cells are present on a side of a layer of the matrix facing the hollow mold.

20. The method as claimed in claim 1, further comprising the step of lining the hollow mold with a support grid or support frame prior to performing steps a)-c).

* * * * *

UNITED STATES PATENT AND TRADEMARK OFFICE
CERTIFICATE OF CORRECTION

PATENT NO. : 10,500,306 B2
APPLICATION NO. : 14/367247
DATED : December 10, 2019
INVENTOR(S) : T. Aper et al.

It is certified that error appears in the above-identified patent and that said Letters Patent is hereby corrected as shown below:

On the Title Page

Item (71) The applicant should read "Medizinische Hochschule Hannover"

Signed and Sealed this
Fifteenth Day of September, 2020

Andrei Iancu
*Director of the United States Patent and Trademark Office*